(12) United States Patent
Zamierowski et al.

(10) Patent No.: US 9,569,566 B2
(45) Date of Patent: Feb. 14, 2017

(54) SIMULATION AND CONTROL SYSTEM AND METHOD USING CONTACT, PRESSURE WAVES AND FACTOR CONTROLS FOR CELL REGENERATION, TISSUE CLOSURE AND RELATED APPLICATIONS

(71) Applicants: David S. Zamierowski, Overland Park, KS (US); Stephen K. Bubb, St. Thomas, VI (US); Wade M. Billings, Lawrence, KS (US); Patrick A. Hildebrandt, Lenexa, KS (US); Eric J. Tobaben, Lawrence, KS (US)

(72) Inventors: David S. Zamierowski, Overland Park, KS (US); Stephen K. Bubb, St. Thomas, VI (US); Wade M. Billings, Lawrence, KS (US); Patrick A. Hildebrandt, Lenexa, KS (US); Eric J. Tobaben, Lawrence, KS (US)

(73) Assignee: Zam Research LLC, Overland Park, KS (US)

( * ) Notice: Subject to any disclaimer, the term of this patent is extended or adjusted under 35 U.S.C. 154(b) by 116 days.

(21) Appl. No.: 13/712,872

(22) Filed: Dec. 12, 2012

(65) Prior Publication Data
US 2013/0151223 A1 Jun. 13, 2013

Related U.S. Application Data
(60) Provisional application No. 61/569,439, filed on Dec. 12, 2011.

(51) Int. Cl.
*G01N 33/48* (2006.01)
*G01N 33/50* (2006.01)
(Continued)

(52) U.S. Cl.
CPC ........ *G06F 17/5009* (2013.01); *A61M 1/0088* (2013.01); *G06F 19/12* (2013.01);
(Continued)

(58) Field of Classification Search
None
See application file for complete search history.

(56) References Cited

U.S. PATENT DOCUMENTS 221,427 A 11/1879 Sherman
1,355,846 A 10/1920 Rannells
(Continued)

FOREIGN PATENT DOCUMENTS

AU 550575 8/1982
AU 745271 12/2002
(Continued)

OTHER PUBLICATIONS

Transducer. The Penguin Dictionary of Physics, 2009, 2 pages. Retrieved online on Nov. 12, 2013 from <<http://www.credoreference.com>>.*
(Continued)

*Primary Examiner* — Russell S Negin
(74) *Attorney, Agent, or Firm* — Law Office of Mark Brown, LLC; Mark E. Brown

(57) ABSTRACT

A description of a device and method of use are provided for a containment chamber, accompanying sensing and monitoring instrumentation, and method of creation of a physical force wave that would be capable of mimicking physiologic waves such as pulse pressure, muscle contraction, peristalsis, acoustic waves and other desired waves to be studied. This device allows for the use of various biologic or biologically comparable fluids—alone or in combination—that would allow for the analysis of the passage of these waves through these media. Singularly, this device also allows for
(Continued)

the manipulation of the external constraints that mimic the containment of that media in vivo. This allows for the analysis of the effects on the nature of the wave, its reflections, potential augmentation or dampening that occur in conjunction with various selected external and internal (baffle) constraints that mimic those found in nature or in therapeutic interventions.

2 Claims, 10 Drawing Sheets

(51) Int. Cl.
G06F 17/50 (2006.01)
G06F 19/00 (2011.01)
G06F 19/12 (2011.01)
A61M 1/00 (2006.01)

(52) U.S. Cl.
CPC ... *G06F 19/3437* (2013.01); *A61M 2205/332* (2013.01); *A61M 2205/3344* (2013.01)

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,648,692 A | 3/1972 | Wheeler |
| 3,682,180 A | 8/1972 | McFarlane |
| 3,826,254 A | 7/1974 | Mellor |
| 3,880,164 A | 4/1975 | Stepno |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,233,969 A | 11/1980 | Lock et al. |
| 4,245,630 A | 1/1981 | Lloyd et al. |
| 4,248,232 A | 2/1981 | Engelbrecht et al. |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,339 A | 8/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,696,301 A | 9/1987 | Barabe |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,775,909 A | 10/1988 | Inoue |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,152,757 A | 10/1992 | Eriksson |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes et al. |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,678,564 A | 10/1997 | Lawrence et al. |
| 5,716,360 A | 2/1998 | Baldwin et al. |
| 5,738,686 A | 4/1998 | Kubein-Meesenburg |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |

(56) References Cited

U.S. PATENT DOCUMENTS

| | | | |
|---|---|---|---|
| 6,146,423 A | 11/2000 | Cohen et al. | |
| 6,159,246 A | 12/2000 | Mendes et al. | |
| 6,174,306 B1 | 1/2001 | Fleischmann | |
| 6,179,804 B1 | 1/2001 | Satterfield | |
| 6,190,391 B1 | 2/2001 | Stubbs | |
| 6,190,392 B1 | 2/2001 | Vandewalle et al. | |
| 6,203,563 B1 | 3/2001 | Fernandez | |
| 6,234,990 B1 | 5/2001 | Rowe et al. | |
| 6,241,747 B1 | 6/2001 | Ruff | |
| 6,258,075 B1 | 7/2001 | Taylor et al. | |
| 6,270,517 B1 | 8/2001 | Brotz | |
| RE37,358 E | 9/2001 | Del Rio et al. | |
| 6,287,316 B1 | 9/2001 | Agarwal et al. | |
| 6,293,929 B1 | 9/2001 | Smith et al. | |
| 6,345,623 B1 | 2/2002 | Heaton et al. | |
| 6,355,215 B1 | 3/2002 | Poggie et al. | |
| 6,377,653 B1 | 4/2002 | Lee et al. | |
| 6,398,767 B1 | 6/2002 | Fleischmann | |
| 6,430,427 B1 | 8/2002 | Lee et al. | |
| 6,488,643 B1 | 12/2002 | Tumey | |
| 6,493,568 B1 | 12/2002 | Bell et al. | |
| 6,500,209 B1 | 12/2002 | Kolb | |
| 6,503,281 B1 | 1/2003 | Mallory | |
| 6,540,705 B2 | 4/2003 | Norstrem et al. | |
| 6,553,998 B2 | 4/2003 | Heaton et al. | |
| 6,589,285 B2 | 7/2003 | Penenberg | |
| 6,620,132 B1 | 9/2003 | Skow | |
| 6,626,891 B2 | 9/2003 | Ohmstede | |
| 6,645,226 B1 | 11/2003 | Jacobs et al. | |
| 6,685,681 B2 | 2/2004 | Lockwood et al. | |
| 6,695,823 B1 | 2/2004 | Lina et al. | |
| 6,726,706 B2 | 4/2004 | Dominguez | |
| 6,752,794 B2 | 6/2004 | Lockwood et al. | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,828,468 B2 | 12/2004 | Ansmann et al. | |
| 6,856,821 B2 | 2/2005 | Johnson | |
| 6,860,903 B2 | 3/2005 | Mears et al. | |
| 6,953,480 B2 | 10/2005 | Mears et al. | |
| 6,991,643 B2 | 1/2006 | Saadat | |
| 7,108,683 B2 | 9/2006 | Zamierowski | |
| 7,381,211 B2 | 6/2008 | Zamierowski | |
| 7,645,269 B2 * | 1/2010 | Zamierowski | 604/305 |
| 2001/0011169 A1 | 8/2001 | Taylor et al. | |
| 2002/0022861 A1 | 2/2002 | Jacobs et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0191443 A1 | 10/2003 | Taylor et al. | |
| 2004/0006263 A1 * | 1/2004 | Anderson | A61B 5/01 600/364 |
| 2005/0089578 A1 * | 4/2005 | Werkmeister et al. | 424/489 |
| 2007/0066945 A1 * | 3/2007 | Martin | 604/313 |
| 2012/0078379 A1 * | 3/2012 | Zamierowski | 623/23.72 |

FOREIGN PATENT DOCUMENTS

| | | |
|---|---|---|
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| DE | 19844355 | 4/2000 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| GB | 692578 | 6/1953 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | WO-80/02182 | 10/1980 |
| WO | WO-90/11795 | 10/1990 |
| WO | WO-93/09727 | 5/1993 |
| WO | WO-94/20041 | 9/1994 |
| WO | WO-96/05873 | 2/1996 |
| WO | WO-97/18007 | 5/1997 |
| WO | WO-99/13793 | 3/1999 |
| WO | WO-01/85248 | 11/2001 |
| WO | WO-01/89431 | 11/2001 |
| WO | WO-03/092620 | 11/2003 |

OTHER PUBLICATIONS

"PCT/GB95/01983", International Search Report, Nov. 23, 1995.

"PCT/GB96/02802", PCT International Examination and Search Report; Jan. 15, 1998 and Apr. 29, 1997.

"PCT/GB96/028202 International Application", PCT Written Opinion, Sep. 3, 1997.

"PCT/GB98/02713 International Application", PCT Written Opinion, Jun. 8, 1999.

"PCT/GB98/02713", PCT International Search Report, Jan. 8, 1999.

Argenta, Louis C., et al., "Vacuum-Assisted Closure: A New Method for Wound Control and Treatment: Clinical Experience", *Annals of Plastic Surgery*, vol. 38, No. 6, Jun. 1997, 563-576.

Blackburn, II, MD, James H., "Negative-Pressure Dressings as a bolster for Skin Grafts", *Annals of Plastic Surgery*, vol. 40, No. 5, May 1998, 453-457.

Dattilo, Jr., Philip P., et al., "Medical Textiles: Application of an Absorbable Barbed Bi-directional Surgical Suture", *Journal of Textile and Apparel, Technology and Management*, vol. 2, Issue 2, Spring 2002, 1-5.

Davydov, Yu A., et al., "Bacteriological and Cytological Assessment of Vacuum Therapy of Purulent Wounds", *Vestnik Khirurgi*, Oct. 1998, 48-52.

Davydov, Yu A., et al., "Concepts for the Clinical-Biological Management of the Wound Process in the Treatment of Purulent Wounds by Means of Vacuum Therapy", *Vestnik Khirurgi*, Jul. 7, 1980, 132-136.

Davydov, Yu A., et al., "Vacuum Therapy in the Treatment of Purulent Lactation Mastitis", *Vestnik Khirurgi*, May 14 1986, 66-70.

Greer, S. E., et al., "The Use of Subatmospheric Pressure Dressing Therapy to Close Lymphocutaneous Fistulas of the Groin", *British Journal of Plastic Surgery* (2000), 53, Article No. BJPS2000, 3360,484-487.

Johnson, Frank E., "An Improved Technique for Skin Graft Placement Using a Suction Drain", *Surgery, Gynecology & Obstetrics*, vol. 159, (Dec. 1984),585-586.

Kostyuchenok, B. M., et al., "Vacuum Treatment in the Surgical Management of Purulent Wounds", *Vestnik Khirugi*, Sep. 1986, 18-21.

Letsou, M.D., George V., et al., "Stimulation of Adenylate Cyclase Activity in Cultured Endothelial Cells Subjected to Cyclic Stretch", *Journal of Cardiovascular Surgery*, 31, 1990, 534-539.

Masters, John "Letter to the Editor", *British Journal of Plastic Surgery*, vol. 51(3), 1998; Elsevier Science/The British Association of Plastic Surgeons, UK, 267.

Mendez-Eastman, RN, Susan "When Wounds Won't Heal", *RN*, Jan. 1998, vol. 61(1), Medical Economics Company, Inc., Montvale, NJ, USA, 20-24.

Orringer, Jay et al., "Management of Wounds in Patients with Complex Enterocutaneous Fistulas", *Surgery, Gynecology & Obstetrics*, vol. 165, Jul. 1987, 79-80.

Yusupov, Yu N., et al., "Active Wound Drainage", *Vestnik Khirurgi*, vol. 138, Issue 4, 1987, 42-46.

\* cited by examiner

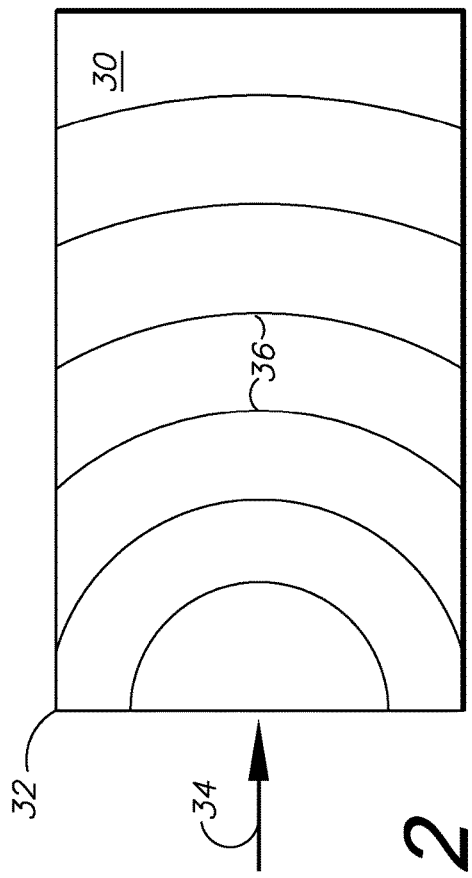
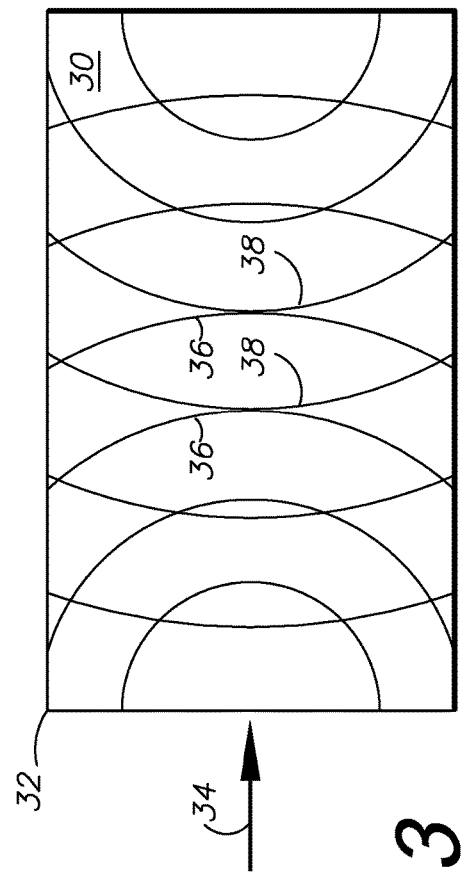
FIG. 2
FIG. 3

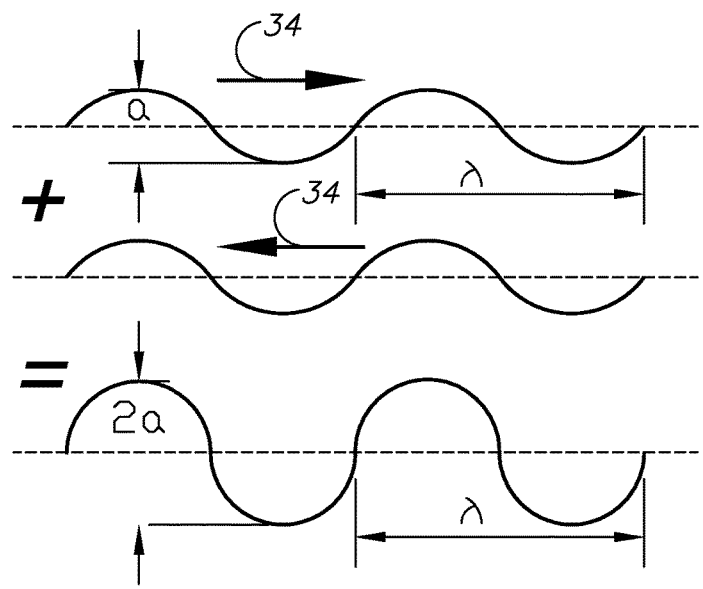
FIG. 3a
FIG. 3b
Reinforced
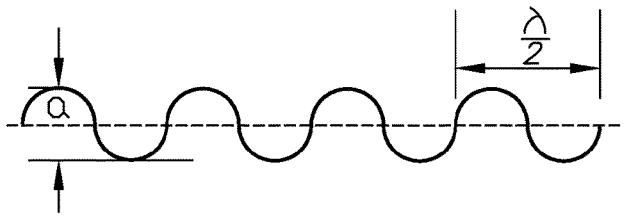
FIG. 3c
Reflected

SIMULATION AND CONTROL SYSTEM AND METHOD USING CONTACT, PRESSURE WAVES AND FACTOR CONTROLS FOR CELL REGENERATION, TISSUE CLOSURE AND RELATED APPLICATIONS

CROSS-REFERENCE TO RELATED APPLICATION

This application claims priority in and incorporates by reference U.S. Patent Application Ser. No. 61/569,439, filed Dec. 12, 2011.

BACKGROUND OF THE INVENTION

1. Field of the Invention

The present invention relates generally to a device and method for simulating and analyzing transmitted physical force waves in diverse media, said media being comparable with various biological fluids and said device allowing for the control and manipulation of the various internal and external constraints controllably applied to that media.

2. Description of the Related Art

Biologic and physiologic systems for mammals have two circulations—the vascular and the lymphatic. At the terminal loops of these two systems we have all elements in close proximity, microscopically close. Previous physiologic studies of this terminal bed at microscopic level essentially just show summary effects, such as flow variations—and then, only in the vascular, red-cell-filled portion of the circulation. Histological exam of this terminal set of circulatory loops clearly shows the vascular, red-cell loops to be continuous from afferent to efferent but the lymphatics start as blunt end channels. Fluid exchange between them is ubiquitous but it is known from clinical and experimental evidence that if the pulsatile nature of arterial flow is dampened or lost, then lymphatic flow stops. The exact nature of this relationship is so far minimally investigated. It is extremely challenging to get in vivo, invasive or non-invasive, instrumentation into these systems at microscopic levels and to sort out the intertwined signals and messages of this complex network of vessels and pulses and flows. Because of that, we propose a "bench-top" simulation for meaningful analysis of the elements and components of this biological system in isolation, allowing controlled variation and study of the potential relationships with the long term vision of being able to re-apply them in vivo.

An average human peripheral pulse pressure at the level of a major named artery is about 110-120/70-80 mmHg giving a pulse pressure of 40 Torr and a mean pressure of 90-100 Torr. This pressure wave decreases as we move peripherally and the mean pressure decreases to approximately 32 Torr as the afferent arteriole enters the terminal capillary loop where it filters extracellular and interstitial fluid as it passes through this capillary loop resistance and the pressure is generally a 20 mmHg drop across the loop and average pressure at the beginning of the efferent venous channel is 12 mmHg with no or a minimally detectable pulse differential. At this level, the blunt end of the lymphatic capillary is collecting this filtrate and starting its flow at a pressure of roughly 7 mmHg. Downhill gradients therefore exist in this system. However, we know that without a pulsating arterial system, flow ceases or is very ineffective in this early lymphatic collection.

Most of these interactions take place in an environment fluidically that is very complex, consisting of liquids of various oncologic and osmotic pressures and concentrations, some with and some without cells, inside of these circulatory vessels or channels. And these vessels, then, are in direct apposition to, in fact they are bathed in or embedded in, an environment of a visco-elastic matrix of fiber and cells suffused in its interstices with this interstitial and extracellular fluid. For simplicity and the ability to analyze components, we will refer to the intra-vessel component as "liquid" and the material outside the vessels as "gel."

Two areas of note in the body have a different fluid distribution. The first is the chest or thorax portion of the body with its ribbed, buttressed walls and its muscular diaphragm able to generate its own separate set of pressure and thus inspire and expire air. So this section of the body interfaces gas with these liquids and gels. The other is bone where we have a porous solid filled with liquids. Our device interfaces with all these states of fluidity.

The human body is highly compartmentalized and specialized. If we look at the body in all its complexity, its different tissue types and organs, its functional "systems," its solid and hollow viscera, etc., the permutations seem almost unlimited. But based on repeating patterns of compartments, there are actually just a few types that we need to consider. If we look at the extremities, for example, we see the outer layer of skin that we will refer to as the "external constraint." Inside this we have several clearly identifiable major chambers of strong, more fibrous, less yielding walls called fascia. We reproducibly, predictably have the deep fascia which parallels the skin and separates the "superficial" and "deep" compartments of the extremity. This compartment layer forms a circumferential layer around all the extremities and the trunk of the body. Inside this layer of deep fascia in the extremities, we have one or two bones centrally and strong separating layers called "intermuscular septi" that join the bone to the deep fascia creating two or three compartments depending on the location. Inside each of these compartments, then, we have additional layers, less strong or thick but still less elastic than the skin, that surround and contain or compartmentalize the muscle groups and the neurocirculatory bundles—which include the larger lymph collecting channels. We will refer to all of these internal, fascial, compartment-producing layers as "internal constraints."

If we look at the thorax or chest, we have gas against the circulatory channels and a more rigid external wall. In the abdomen then we have relatively thin hollow tubes, the intestines, filled with liquid. This is a much different liquid to gel ratio than we find in the extremities. And in the abdomen we have larger more distinct circulatory channels not in compartments but in thin membranes (mesentery) in essentially direct contact with the viscera around them and with the large aortic pulse behind them.

Considering how these elements are arranged and manipulated to achieve special circumstances in circulation, multiple examples are found. Based on the premise that a pressure wave is necessary for (lymphatic) flow, we see this arranged in a variety of patterns: first, for example, with arterial pulsation intimately intertwined with the "two circulations" in peripheral and terminal vascular beds; then we also see it in enclosed neuro-vascular compartments (internal constraints) in the extremities along the paths of major longitudinally arrayed vessels. We see it combined in compartments with different types of pressure waves: muscular action produces a compressive wave in the muscle compartments of the extremity; the slow undulating wave of peristalsis, or abdominal hollow visceral contraction, is yet another type of pressure wave that the vessels are exposed to and compartmentalized with. One of the most dramatic, and applicable examples for our purposes, is the interspecies mammalian differences between, on the one hand, a human forearm, in which the skin is thin, supple and elastic, and in an individual with low body fat, allows us to see the veins bulging out, pushing the skin with just 10 Torr, and then the tissue tenting inward (at transiently created negative pressure because of the change in surface area and volume in relation to ambient air pressure) between the outward protruding pairs of flexed tendons, and, on the other hand, the thick, non-flexible or minimally elastic skin of the giraffe's ankle which aids in the return of blood up a significant height back to the right atrium of the heart and aids in maintenance of the correct filtration pressures given the size of the heart pump in the giraffe which is twice the size of mammals of similar weight.

These examples of the variation of external constraint have direct clinical application and constitute requirements for the construction of our device. We want to be able to manipulate the external constraints on our device to mimic at least the four major types of clinically applied external dressings or garments that are felt to have vascular (flow) effects: 1) rigid, immobile, closely-applied dressing (at least non-elastic if not rigid), e.g. "contact casting" for diabetic foot wounds, orthopedic casting for trauma, Unna boot for stasis ulcers; 2) flexible, elastic single or multilayer wrap, e.g. Jones wrap, 2 or 3-layer compression wraps for stasis disease, ace wrap for athletic injuries; 3) air or water filled compression wraps (positive pressure), e.g. "G suits," MAST trousers for trauma, compression garments for venous stasis disease; and 4) vacuum-press applied dressings (negative pressure), e.g. compressed-foam suction applied external dressings such as the VAC, or external suction dressings with other materials.

The effects that changing volume and surface area inside a space can have on fluid dynamics and vice-versa are well known. Ideally, a device to duplicate physiologic states should have this ability to change volumes by manipulating the external constraints and changing the internal pressures independently.

An area of wound-dressing and wound-healing technology is known as "moist wound healing." Three major components that constitute the external and physical environment of the healing wound should, in an ideal wound-healing environment, be controlled. First, wound healing is inversely related to bacterial growth. Second, it has been shown that, holding other variables constant, there is a clear linear relationship between the moisture level at the wound-site and the rate of epithelial advancement. The final important characteristic is the surface contact property of the wound dressing. The surface contact property can help to control the other two major factors, but must be made of a suitable material that promotes endurance of the dressing as well as comfort to the patient.

Thin pieces of foam have been used in moist-wound healing applications. The external face of the thin foam was more open allowing for enough moisture retention initially, but then allowing drying to occur with the dressing still in place. Because this foam did not adhere to the wound, it could be moved or removed without disrupting the epithelium. However, this practice was often limited to use with incisions smaller than one inch, as the thin foam is incapable of managing a large amount of exudates for a large, fresh wound, and if exudates accumulate under the foam piece the foam will lose surface contact, which allows bacteria to build up.

In general, epithelium advances or migrates best if moisture is maximized and then matures best if moisture is minimized. Although the idea of moist wound healing is not new, it is still evolving.

Another important aspect of wound healing relates to the respective roles of the vascular and lymphatic circulatory systems, both of which are involved in wound healing, but perform different functions. An injury to the vascular system typically results in clotting due to the exposed red blood cells, which controls bleeding. Lymph fluid, however, lacks comparable coagulating properties. Moreover, the lymphatic circulatory system lacks the muscled walls of the vascular circulatory system. Stemming the outpouring of lymph, interstitial fluid and white cells involves compressing the lymphatic circulatory system through surrounding tissue swelling from an accumulation of edema and interstitial fluid. Unlike the quick response of coagulating red cells, lymphatic circulatory system closure tends to be slower and can take days.

Based on the involvement of the vascular and lymphatic circulatory systems in wound healing, influencing the performance of these circulatory systems can significantly improve wound healing. Wound closure can be achieved more quickly and infection risks can be reduced by controlling the factors affecting vascular and lymphatic circulation. For example, a profusion of blood flow in the wound site generally promotes re-epithelialization. The cells are also responsive to compression and tension. Properly applied and sequenced, compression and tension can promote healing.

The present invention addresses these wound healing factors by controlling and directing cellular functions based on contact and controlling such physical forces as shear, compression, tension and other physiological variables associated with the tissues and the fluids associated with the wound site and otherwise involved in the wound healing process.

SUMMARY OF THE INVENTION

In embodiments of the invention, cellular contacts are simulated and controlled through the application of various factors, including contact relationships and forces. A unique dressing and treatment method accomplishes the objectives of enhancement and protection of (re)epithelialization, both migration and maturation, without disruption of the fragile layer by undue adherence or by motion/friction/abrasion and yet maintaining the closest of surface contacts without intervening dead space (or its consequence of fluid accumulation, lytic bleeding, and micro abscess formation and lack ultimately of the ability to dry and mature epithelium) by drawing away air and liquid from the wound and introducing fresh air and fresh liquid to the wound to expedite healing. In this embodiment, air and moisture levels at the wound-site can be balanced by using vacuum pumps to remove excess air or moisture, and input pumps can be used to add additional clean air, moisture, or other elements which enhance healing. The vacuum pump may also provide negative pressure to press the dressing against the wound and enhance healing.

BRIEF DESCRIPTION OF THE DRAWINGS

FIG. 2 is a diagram of a pressure wave transmission in a medium.

FIG. 3 is a diagram of opposing pressure waves in a medium, which can be created by an impact(s) on a media containment, such as a living organism or a vessel. An opposing pressure wave can also be reflected by the containment.

FIG. 3a shows synchronized pressure waves in a medium, which result in a reinforced, standing pressure wave as shown in FIG. 3b.

FIG. 3c shows a reflected pressure wave condition with increased frequency and shorter wavelength.

DETAILED DESCRIPTION OF THE PREFERRED EMBODIMENTS

I. Introduction and Environment

As required, detailed aspects of the disclosed subject matter are disclosed herein; however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. Said terminology will include the words specifically mentioned, derivatives thereof and words of similar meaning.

II. Embodiments and Aspects of the Invention

Figure 1:
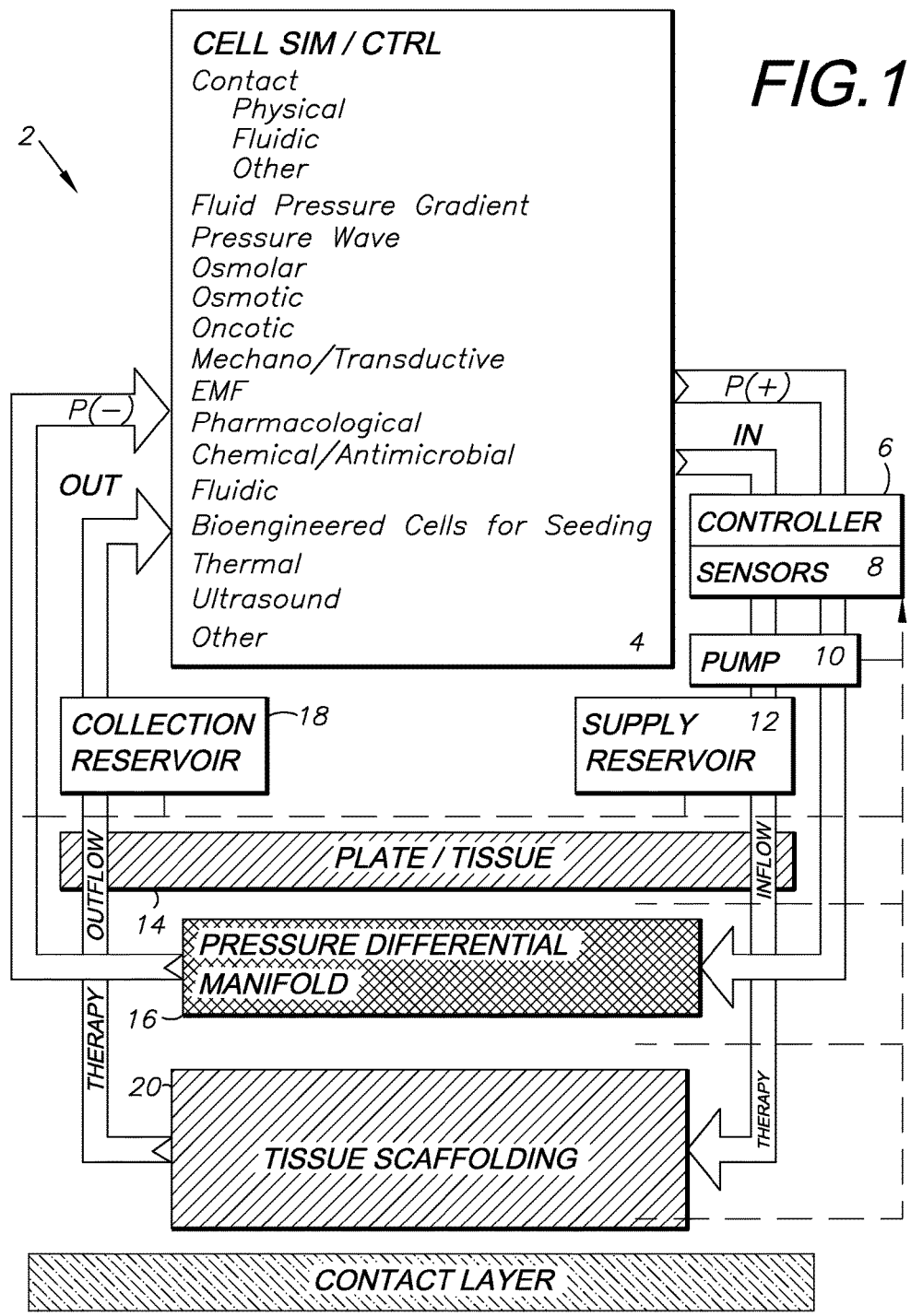
FIG. 1 is a schematic diagram of a cellular simulation and control system embodying an aspect of the present invention.

FIG. 1 shows a cellular simulation and control system embodying an aspect of the present invention, which is generally designated by the reference numeral 2. The system 2 includes cell simulation and control factors 4, including without limitation: contact (physical, fluidic and other); fluid pressure gradient; pressure wave; osmolar; osmotic; oncotic; mechano/transductive; EMF; pharmacological; chemical/antimicrobial; fluidic; bioengineered cells for seeding; thermal; ultrasound; and other factors, influences and forces. A controller 6, such as a microprocessor, is connected to various sensors 8 and is adapted for preprogramming to control the operation of the system 2. A pump 10, a fluid supply reservoir 12, a plate/tissue element 14, a pressure differential manifold 16, a collection reservoir 18 and tissue scaffolding 20 comprise additional main elements of the system 2. Additional cellular control and tissue regeneration systems and methods are described in U.S. Patent Publication No. 2012/0078379, which is incorporated herein by reference.

FIG. 2 shows a pressure wave medium 30 within a container 32, which can be subjected to an external force depicted by a force arrow 34. Pressure waves 36 are shown in the container 32. FIG. 3 shows the container 32 with reflected pressure waves 38 in the medium 30. The container 32 and the medium 30 contained therein can be chosen for desired performance characteristics, such as simulating human tissue. FIG. 3a shows combining synchronized pressure waves, which can be moving in opposite directions indicated by arrows 34, resulting in a reinforced pressure wave as shown in FIG. 3b, with twice the amplitude a and the same wavelength and frequency. Various containment and "backwall" conditions can be involved in an in vivo condition, which can affect the force/pressure waves. For example, FIG. 3c shows a reflected wave consideration with twice the frequency, half the wavelength and the same amplitude. Of course, incident and reflected waves can be combined at various angles and timing for achieving desired pressure wave effects. Moreover, the waves can represent fluid pressures, physiological conditions, electromagnetic forces (EMF), acoustic, hydrodynamic and other wave forces. Still further, multiple wave sources can be combined and utilized to achieve desired outcomes. For example, enhancing tissue growth, regeneration, healing and circulation of both blood and lymphatic fluid can be achieved with the present invention, for facilitating positive outcomes with enhanced results.

Figure 4:
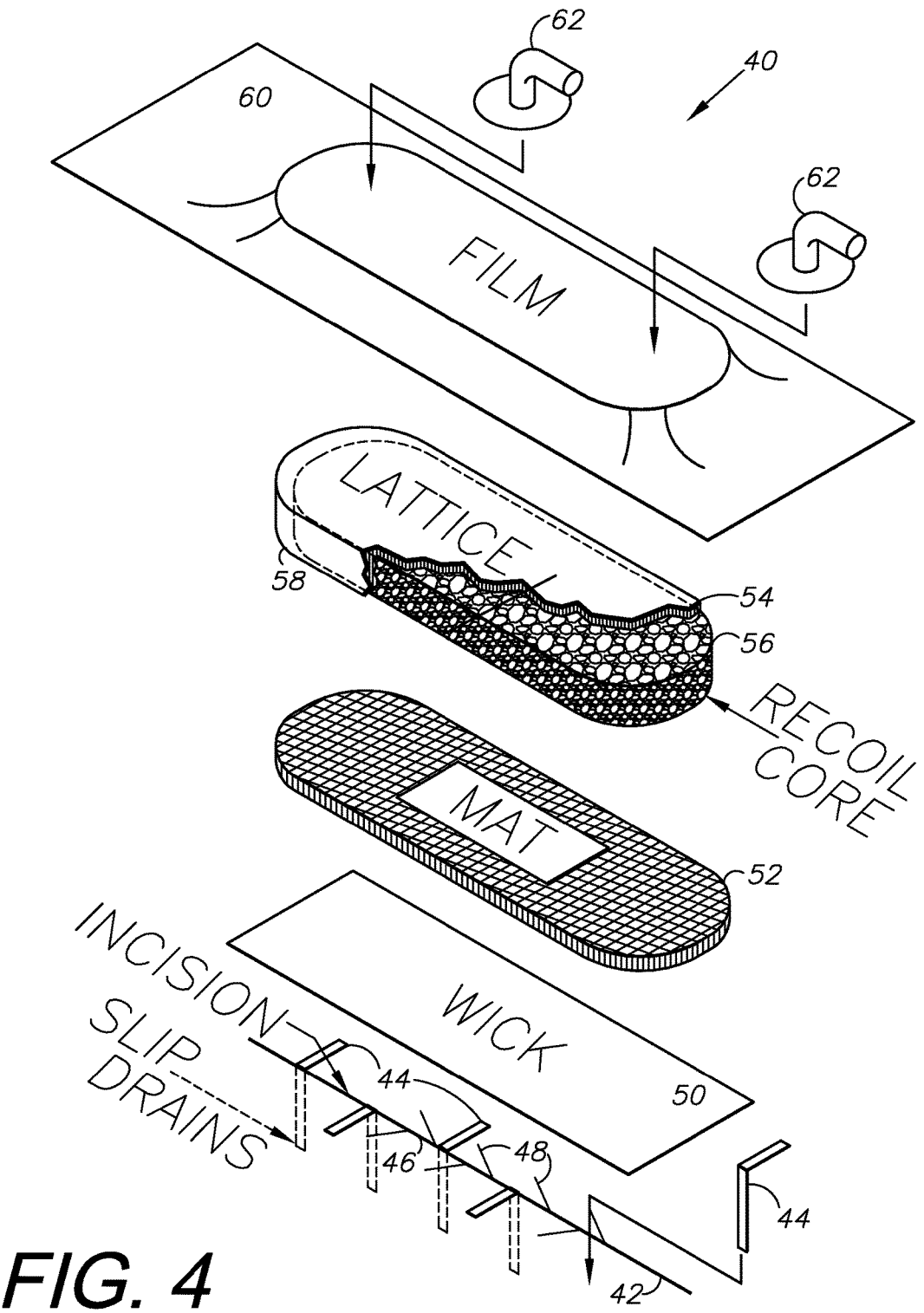
FIG. 4 is an exploded diagram of an externally-applied wound dressing for placement on an incision and utilizing the system and method of the present invention.

FIG. 4 shows an external dressing 40 adapted for application over an incision 42, which can have slip drains 44 placed between the separated tissue portions to facilitate drainage of the closed wound 46. The wound 46 can be closed by sutures 48 or other closures, such as staples, adhesive, etc. A wick material 50 can be placed over the incision 42 and covered with a mat 52. A composite fluid transfer element 54 includes a recoil core 56, such as a polyurethane, open-cell foam material, and a fluid-wicking lattice 58 placed thereover. A film cover 60 is placed over the fluid transfer element 54 and can comprise a semi-permeable membrane or other suitable cover material. Fluid connectors 62 are attached to the film cover 60 and are adapted for connection to fluid transfer conduits, tubing, etc.

Figure 5:
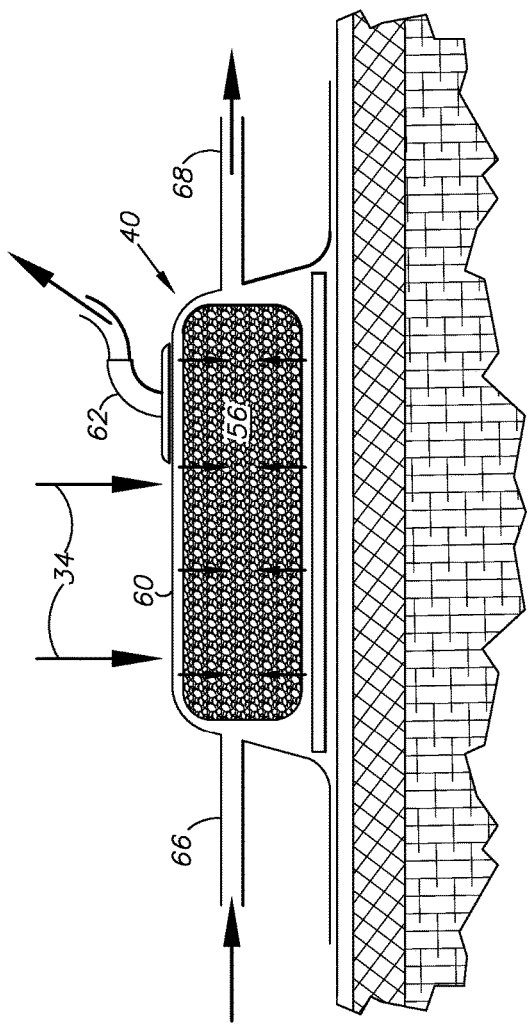
FIG. 5 is a cross-sectional view of the external dressing, showing ambient air and negative pressure force vectors, along with fluid flow through the dressing.
Figure 6:
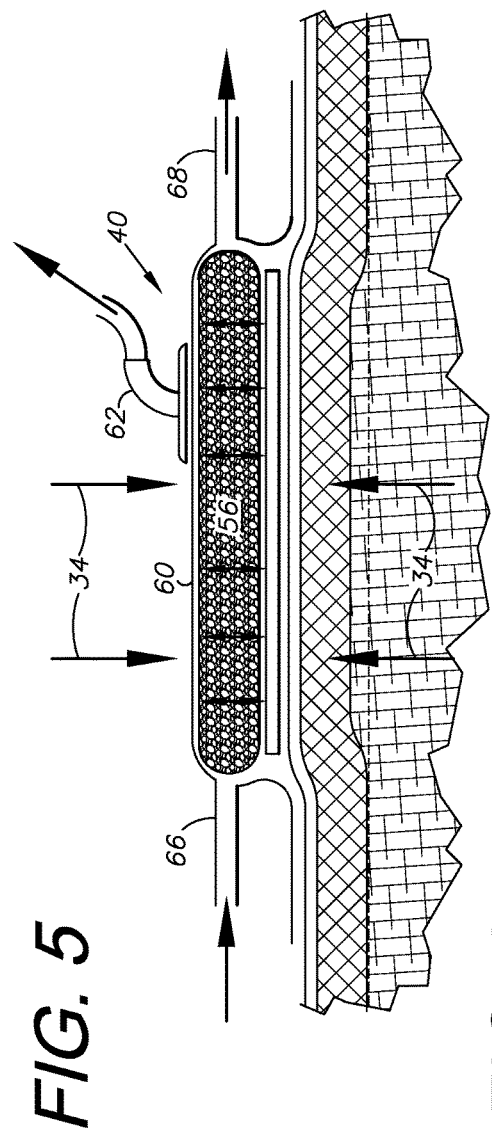
FIG. 6 is another cross-sectional view of the external dressing showing the component relationships and the effects of various forces acting on the system.
Figure 7:
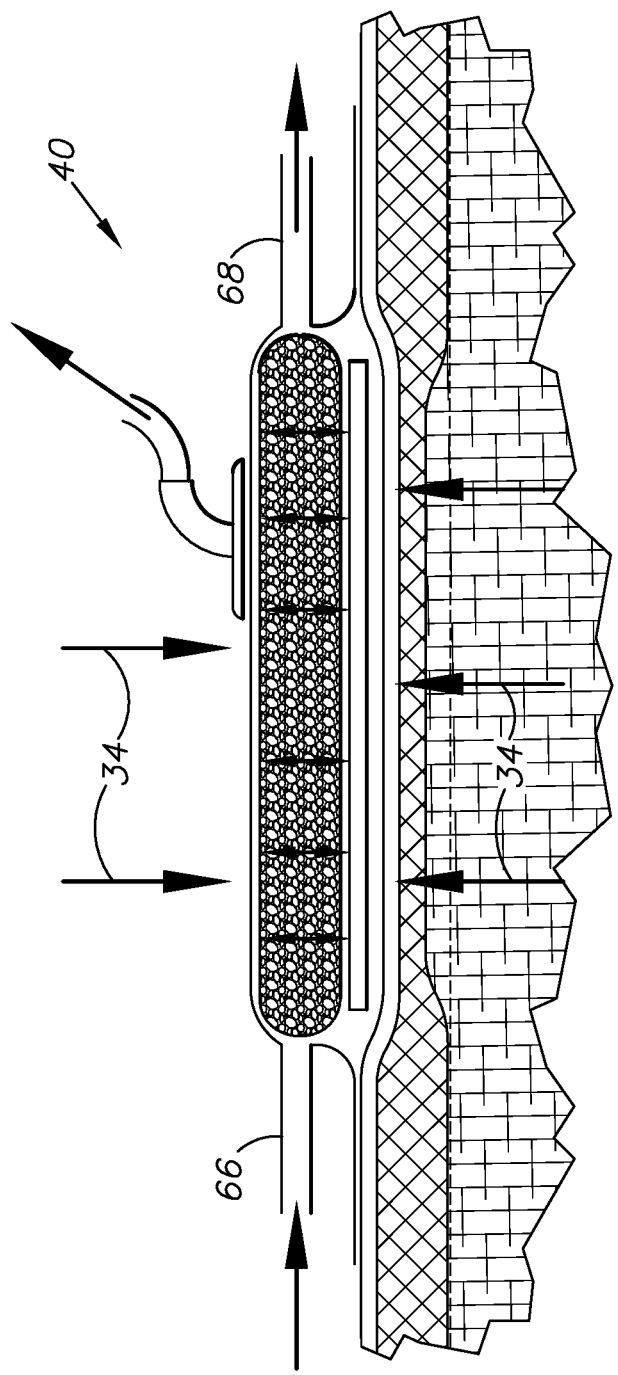
FIG. 7 is yet another cross-sectional view of the external dressing showing an uplifting effect on underlying tissue.

FIGS. 5-7 show the external dressing 40 applied to a closed wound (e.g., incision 42) through various phases of a healing procedure, including drainage and closure steps, along with various ambient and applied forces represented by force and fluid flow arrows 34. In FIG. 5, the dressing 40 is shown applied to the closed wound 46 with both the dressing 40 and the tissue around the wound 46 in their normal states, i.e., neither compressed nor expanded. As shown by the force arrows 34, ambient air pressure presses down on the dressing cover 60. Suction can be applied via the fluid connectors 62 and fluid inlet and outlet functions are applied at 66, 68. FIG. 6 shows the dressing recoil core 56 compressed and exerting outward pressures corresponding to its compressed state. The underlying tissue, e.g., the fascia layer, is slightly lifted by the negative pressure forces of the dressing 40 above and by the naturally-occurring edema and swelling associated with wounds. Of course, by draining fluid from the wound with negative pressure, swelling and edema are minimized. FIG. 7 shows the underlying tissue layer somewhat compressed by forces from above and below, whereby the dressing 40 may be slightly inset into the epidermis. Of course, scarring, infection and other problems associated with wound healing can be controlled or eliminated by this procedure.

Figure 8:
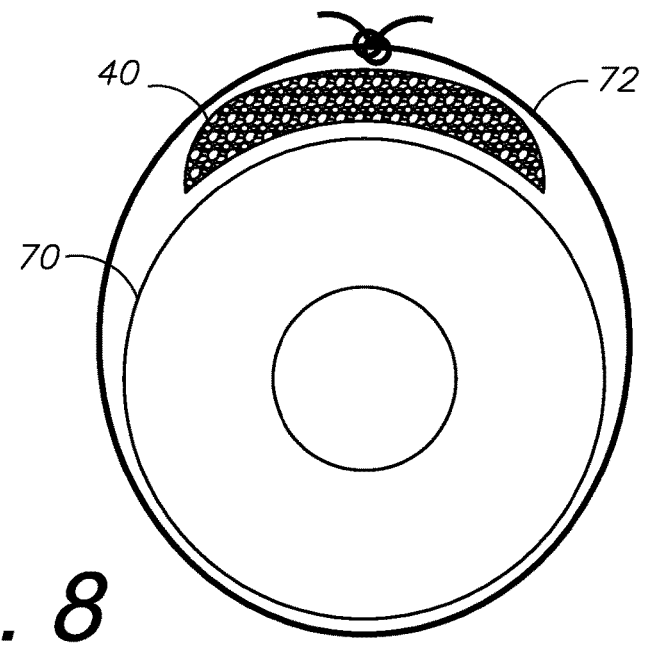
FIGS. 8-10 are diagrams of encircling applications of dressings embodied in aspects of the present invention on a limb, extremity or torso.
Figure 9:
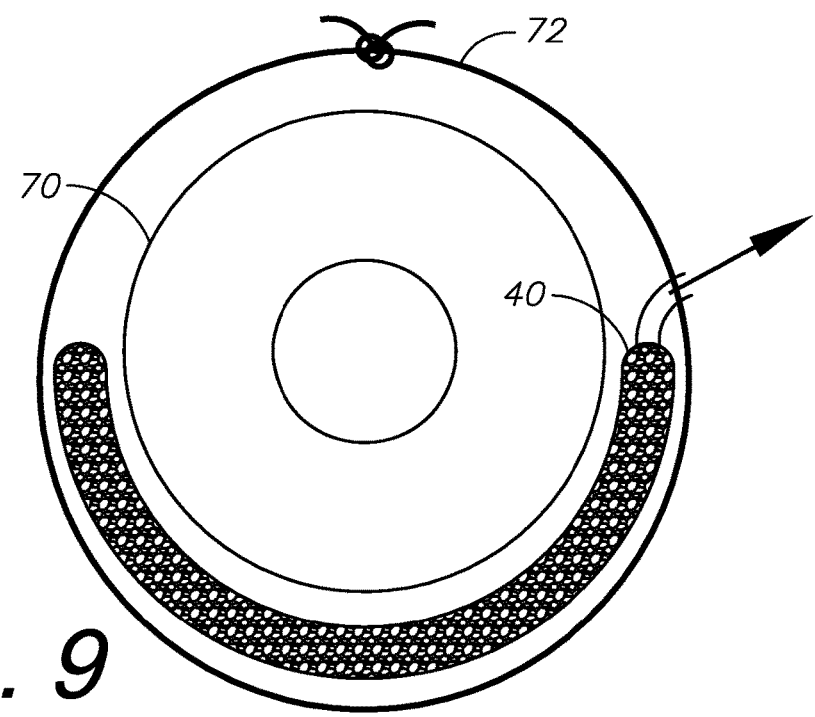
Figure 10:
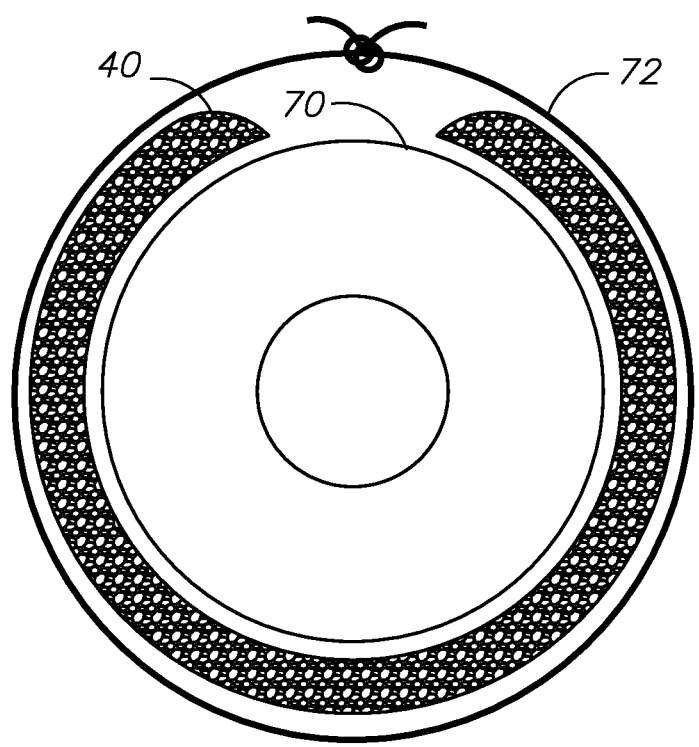

FIGS. 8-10 show configurations of the external dressing 40 circumferentially applied to, for example, a limb 70. As shown, the dressing 40 can be sized to partially encircle the limb 70 to the extent necessary, and can be circumferentially attached, e.g., with an encircling suture 72. Swelling and edema in limb treatment procedures can be effectively controlled by applying negative pressure techniques, controlling fluid and applying suitable antibiotics, growth factors and other pharmacologicals. The forces associated with the dressing 40 can be applied radially inwardly or outwardly as appropriate for particular procedures being performed.

Figure 11:
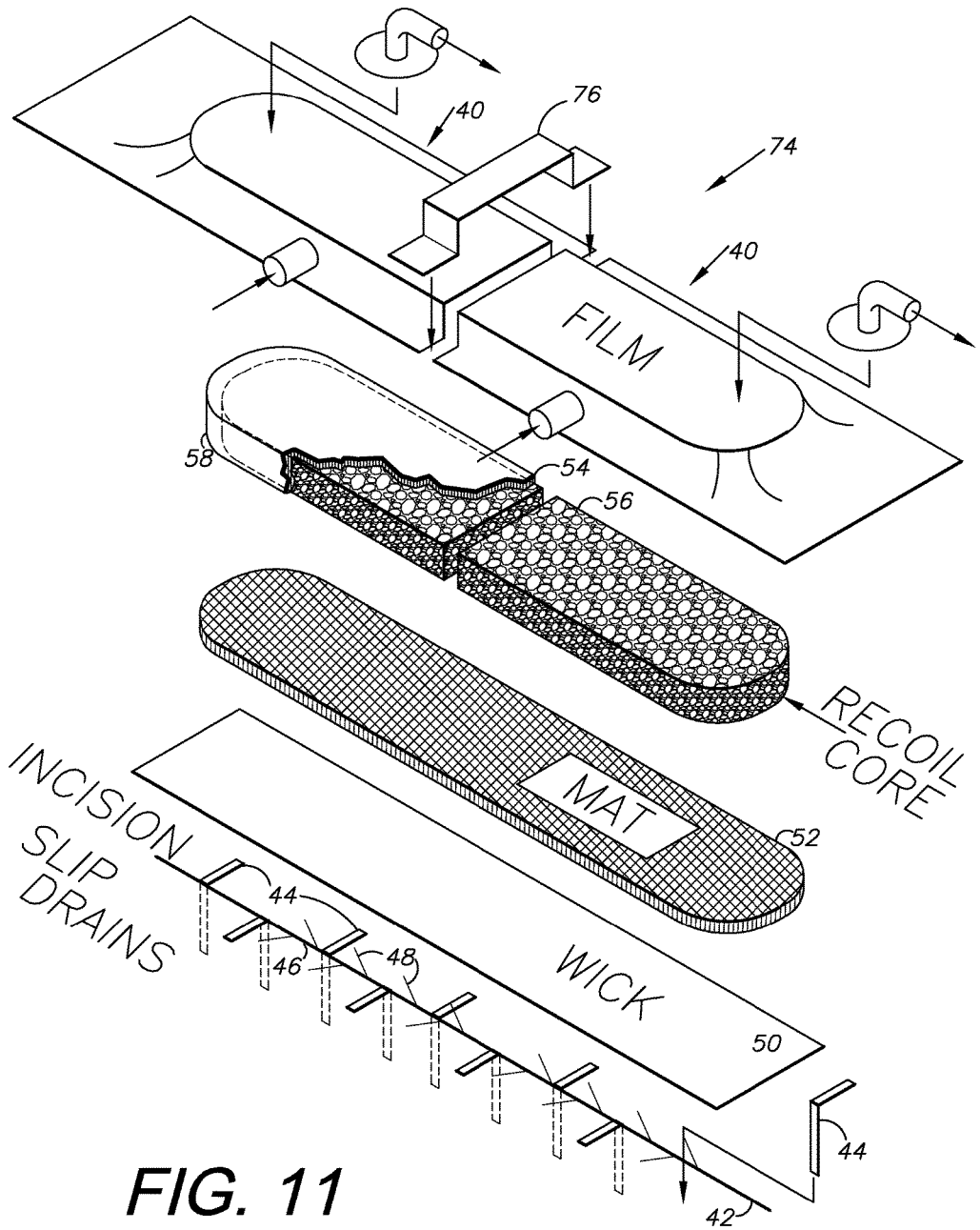
FIG. 11 is an exploded diagram of a dressing system embodying an aspect of the present invention, including a multi-segment recoil core and corresponding film cover.
Figure 12:
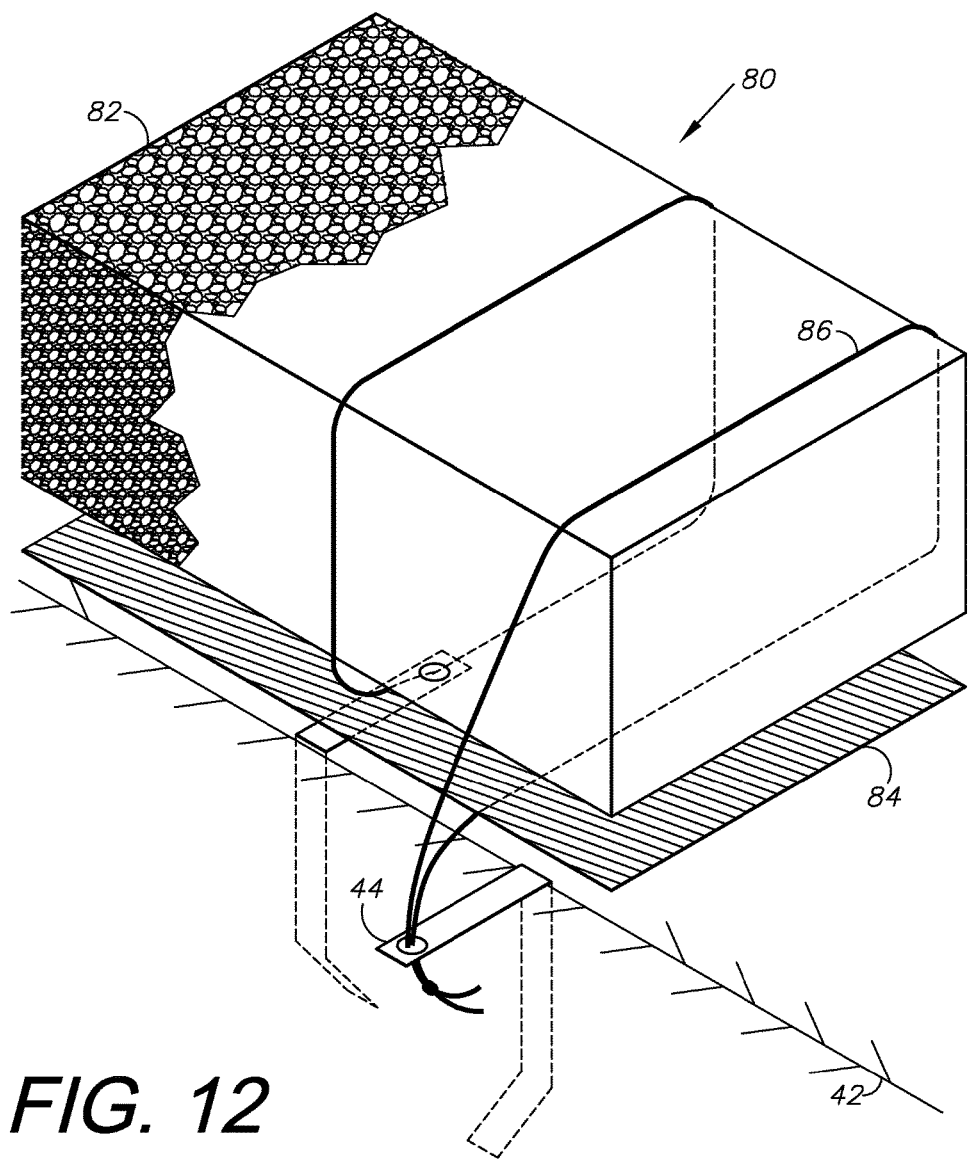
FIG. 12 is a diagram of another alternative embodiment dressing system embodying an aspect of the present invention and using loose suturing for conveying fluid from an incision to a foam manifolding component.

FIG. 11 shows an external dressing 74 comprising multiple individual dressings 40, which can be connected by a connecting strip 76, which can be placed over adjacent ends of individual dressing assemblies 40, which can be combined and configured as appropriate for particular applications. FIG. 12 shows an external dressing 80 including a fluid transfer element 82, which can be placed over a suitable mat or wick material element 84. Sutures 86 can be used to encircle the fluid transfer element 82 and connected to the slip drains 44 whereby fluid can be transferred from the closed wound 46, along the slip drains 44, to the sutures 86 and extracted from the fluid transfer element 82 or its film cover.

III. Dressing Components

Using the embodiments and aspects described above, and variations thereof, tissue, fluid, force and pressure relationships, as well as inter-tissue compartments and other structures defined by the various effected tissues, can be modeled and simulated with just a few configurations of essential components. Examples of certain components, functions and relationships are discussed below.

External Constraint—This can be of any material that will give us the properties we are looking for and in any shape that is suitable. That is, this material can run from rigid walls to elastic or inelastic membrane and the shape can run from box to cylindrical or spherical to amorphous and unconstrained.

Internal Constraint—This, likewise can be of any suitable property and form any convenient shape and produce any desired number of compartments, depending on what one is trying to simulate.

Pulse or pressure wave—Simulating a biological vascular pulse pressure wave by placing elastic tubing in an internal compartment that communicates externally through ports allowing for filling that tubing with liquid in a pulsatile manner, or alternatively, sending a pressure wave through the liquid by compressing the tubing and liquid that is external to the container in a pulse wave like manner (e.g., an external cam-driven roller pump, an internal piston, etc.), that wave then being transmitted via the liquid through the interior of the device. Alternatively, if the external constraint allows for direct access to the internal medium, a mechanical force can be delivered in tension/compression/shear vectors. Acoustical, blast and ballistic forces can similarly be delivered both internally and externally.

Sensing Equipment—This device must be capable of coupling with and/or utilizing the full range of sensing equipment available for evaluating pulse waves, whether by their speed or shape or associated pressure changes or temperature changes or other gradient effects. This equipment includes, but is not limited to: optical devices, with laser or other light sources, with photo-detector or high speed camera; fast response pressure transducers, including "force plates" like that provided by "Tecscan®," all the way to analog hydrostatic manometers for evaluating pressure changes; microphones and other arrays for detecting acoustic level vibrations; heat flux gauges; ionization gauges; strain gauges; other stress gauges. This device and its sensing equipment must be capable of sensing not only the nature of the shock or pulse wave at its origin but the effect of its reflection by variously modulating surfaces (external and internal constraints) while experimentally changing the volume and shape of the fluid contained/constrained by these surfaces.

IV. Embodiment A

This represents the least constrained model. The gel medium is rendered by utilizing synthetic or engineered dynamic gel. This provides the opportunity to cut the material to insert sensors and to shape the material by warming and pouring into containers that produce the desired shape and size for testing. The gel can then be removed from the shaping container and left with just the dependent surface in contact with the supporting structure or the gel can be supported in planned percentages of circumference by netting or slinging.

The internal liquid phase can be simulated by elastic tubing (e.g. Penrose Drain latex tubing in various widths) extended beyond the surface of the gel allowing measured addition, pressurization, pulsation and removal from an external access point to the tubing. This can be placed, as can the sensors, by cutting the gel at the desired point(s) or by pouring the gel to that point, allowing some cooling, laying on of the tubing/sensors, and then pouring the rest of the gel above that to the desired height.

A working example of a different mechanical pulse example would consist of the formation of a gel block in a cylinder shape, placement of the cylinder on-end so that the sides are completely unconstrained, and dividing the gel in half to place tubing/sensors.

A Tecscan® force plate detector can be placed in a center transverse plane, and delivers a reproducible mechanical shock wave pulse to the system by swinging a metal ball of measured weight and size from a given height on a measured suspension band from a predetermined height or angle. The effect on the force plate is recorded over time. The gel cylinder is then wrapped in cellophane (or any material to be tested) and the mechanical pulse wave repeated and the measurements repeated and compared. This is an example of a very simple evaluation of the influence of an external constraint on the behavior of a pulse wave as recorded by a force plate.

A more complex but similar evaluation is to use the same cylinder of ballistic gel and instead of a force plate in the mid-transverse section, we just place another sheet of the same cellophane like material which wraps the external circumference of the cylinder. We use the same mechanical shock wave production but this time we observe the wave directly using laser optics with an instrument like the new SM 690 from Micron Optics. This optical sensing module for ultra-high speed optics and mechanical vibration measurements can be applied to this system for any shock wave or ballistic testing or blast analysis, acoustic emissions monitoring and other vibration-made analyses. This enables us to observe what the reflections are like from the external surfaces but also what the presence of the internal baffle or constraint does to the propagation of the wave from one half of the gel to the other.

V. Embodiment B

This is the most constrained model. Of course, all permutations between A and B are feasible. This model consists of an appropriate rigid material, like acrylic or some other plastic or metal (even the container that the ballistic gel is melted in), that forms the sides of this model. For the example of this embodiment we choose a square shape and rigidly supply 5 of the 6 walls of the cube. The gel is prepared, whole, cut or layered as described above, and poured or placed in the container (or the container can be built around the gel). "Through-hull" type fittings are fashioned with the gel flush with the internal or external portion of the walls and the above described tubing, measuring devices and mechanical force impounder are fitted through them. For example, the lines of the sensors can be run up the walls and over the top of the container or lead out through holes in the wall. A mechanical force piston can be fit in such a hole and separated from the gel by a flexible dam and the mechanical impulse delivered to the gel in this fashion.

The $6^{th}$ wall of the "box" can then serve as the experimental variable. Materials that mimic clinical dressing applications can be applied, flush, with gaps or with pressure, covering the entire surface or just partially—whatever the experimental requirements for analysis. Various pulses can be delivered and the resulting wave effects analyzed as the character of the $6^{th}$ wall is changed. Internal baffling can also be installed. Sensor orientation can be changed.

VI. Embodiment C

This arrangement of components and sensors is like the rigid box in B, however the placement of tubing and sensors is exchanged. The (central) embedded (can either start collapsed or the anticipated average size be cored out of the gel) elastic tubing (utilizing as part of the testing various degrees of elasticity and rigidity) can be continuous throughout the length of the box, containing liquid in the tubing all the way throughout as it runs from input through output ports, ending at valves or sensors or pumps on the exterior of the box. Or it can end blindly in a blunt end within the gel inside the experimental box utilizing only a single port for administering or removing the liquid it contains and for passing the sensors. Instead of sensors in the gel as in Embodiment B, the sensors, e.g., a string of micro manometers in a catheter with the sensors placed every few centimeters or an elongated format for the Tecscan® force plate can be inserted inside the tubing. The upper surface side of the box filled with gel could be completely open, allowing the pressure impulse to be delivered at varying angles over this entire area. This format then is particularly suited to studying the effects of angle variation in the consequent pulse wave delivered to another structure. Conversely, the format in Embodiment B can also be used with the wave impulse delivered from various ports in the sides of the box and/or the position of the internal tubing changed, so that angles could continue to be varied but the surface constraint could now also be varied. Of course, it is an option to visualize the wave by optics, acoustics or Doppler instruments to observe how it hits the target site and, perhaps more importantly, how its reflection from the test surface augments or dampens that wave.

The maze of intertwined circulatory and lymphatic channels provides multiple and reduplicated effects like "waves" that cancel out. Summary measurements are primarily of interest. But changes observed during long in-vivo inspection of an actual functioning circulatory system in Roy and Graham indicate that this system has considerable local control. A parallel exists in fluid dynamics.

A wound, such as an incision, can be prepared by placing an external dressing onto the wound. The dressing promotes healing at three levels of the wound repair continuum: healing (epithelialization) of an open wound, stability of a recently epithelized, but not matured, wound, and maintenance of a mature or intact epithelium without breakdown under a dressing. This dressing device has the unique advantage that it can be applied for a short period of time (days) or left in place without changing for up to six weeks. This is possible because the wound removes old air and liquid from the wound-site and introduces fresh air and liquid to the wound-site to expedite the healing process.

The external dressing can be configured with various components, which can be selected and configured for expediting and optimizing the healing procedure for various closed wounds and patient conditions. By way of non-limiting example, the external dressing includes a surface contact layer or wick comprising a wicking material layer, a mat, a polyurethane foam core with a lattice covering and a semi-permeable film cover overlying the other components.

An optional, perforated tubular deep drain can be placed in or in proximity to the wound and slip drains can optionally be placed in the wound. Suitable, optional closures for the wound include sutures, staples, adhesives, etc.

Alternatively, a suitable direct-contact foam core can be placed directly on the skin surface and simply covered with the membrane film cover. Still further, the foam core can be completely enclosed in a cover layer of a suitable material, such as a wicking material layer. Further still, the dressing can be completely unitary and self-contained for direct placement, whereupon the pressure differential feature described below can fix the dressing to the surrounding, intact skin surface for proper positioning over the wound.

The core can be placed on top of an optional mat, which can be selected to cooperate with the wicking material layer in conveying fluid from the wound. The core can distribute vacuum pressure differential to the surface contact layer. The core is preferably collapsible and flexible and returns to its approximate original size and shape when vacuum pressure is removed. Without limitation, a suitable core material is an open-cell hydrophobic foam material which will maximize the above-listed desirable characteristics of the core. This material can be integrated with the surface contact layer. Other core materials may be used instead, such as hydrophobic foam or hydrophilic fiber matrix pads.

The cover layer covers the other components including the compression core and the surface contact layer. The cover layer is preferably relatively thin and flexible so that it can be collapsed over the underlying core to distribute atmospheric pressure to all covered areas. Suitable, commercially-available, semi-permeable membrane materials are discussed above.

VI. Testing and Data Collection Results

Without limitation on the generality of useful media, gel-type media, such as Perma-Gel available from Perma- Gel, Inc. of Albany, Oreg. (www.perma-gel.com) can be used. The U.S. Department of Defense uses such products, which have been referred to as "ballistic gel," for ordinance and related testing and simulation. This medium was chosen for an experiment to test the effect of external constraint variation on the transmission characteristic seven acoustically-generated pressure wave. The gel was formed into bubble-free cylinders by using a double-boiler technique. An acoustical wave-generator (e.g., audio speaker) and an audio receiver were embedded at opposite, longitudinal ends of the cylinder by a melting and precooling technique. Various wraps and applications were applied to the outside of the circular portion of the cylinder, which was stood on a vertical longitudinal axis for purposes of performing the test.

The results of the tests indicated that, as compared to the unwrapped control state, certain wraps not only produced increased amplitude of the input pressure waves (e.g., 7 kHz square-wave signals), but also produced detectable signals at harmonics of increased frequency (e.g., 14 kHz, etc.). Such higher-frequency reflected wave patterns are illustrated in FIG. 3C. The media (simulated) and living, in-vivo tissue can be enclosed and otherwise constrained with various containment elements, which can be configured and chosen to achieve desired wave patterns in the media. Incident waves can produce reflected ways upon reflecting off containment elements, which can affect amplitude (a), wavelength (λ) and frequency f.

VII. Closed-Wound Treatment Method with Dressing

Pressure changes below the skin surface are provided by the following physiologic functions: a) arterial pulsation, which tends to be amplified by the inelastic characteristic of the dressing coupled and cooperating with the skin; b) muscle contraction, which also tends to be amplified by this inelastic characteristic of the system; and c) the leakage of tissue fluid and the buildup of edema, e.g., intracellular edema.

Edema fluid buildup is the means by which leaking lymphatics are closed by compression. As blood dries and forms clots, the lymphatic vessels tend to be compressed. The dressing facilitates the compression of the lymphatics by amplifying the effects of blood, tissue and edema fluid buildup. Thus, the normal lymphatic system compression response, which can take approximately three days, can be significantly accelerated. Bacteria are cleaned up in the wound site by macrophages and white cells. Epithelial cells begin to move and migrate to the wound site based on the lymphatic system control. The edema formation and inflammation phases of normal wound healing can thus be avoided or at least minimized.

It is to be understood that while certain aspects of the disclosed subject matter have been shown and described, the disclosed subject matter is not limited thereto and encompasses various other embodiments and aspects.

Having thus described the disclosed subject matter, what is claimed as new and desired to be secured by Letters Patent is:

1. A system for simulating an in vivo cellular interaction in a simulated therapy zone and measuring sensed simulated cellular response characteristics for output via an operator interface, which system comprises:
    a medium material including a characteristic simulating an in vivo characteristic, said medium material including an interior forming said simulated therapy zone and an outer surface;
    a container enclosing said medium material outer surface and configured for receiving and containing said medium material;
    said container including external constraints configured to mimic in vivo conditions and for application to said medium material;
    an energy source adapted for exerting a pressure gradient via simulation onto the cell and measuring a response of the cell to the simulated pressure gradient;
    a simulated cell manipulating factor source connected to the medium material and the energy source;
    said simulated cell manipulating factor source being chosen from the group comprising:
    fluid pressure gradient;
    a pressure differential manifold in the simulated therapy zone;
    an inflow line fluidically connecting the factor source to the pressure differential manifold;
    an outflow line from the pressure differential manifold;
    a fluid source connected to the therapy zone via the inflow line;
    a pump connected to the factor source and the inflow line;
    a controller connected to the pump and programmed for controlling the operation of the pump in response to simulated therapy zone conditions;
    said manifold comprising a fluid-permeable foam material and manifold tubing fluidically connected to said foam material;
    said controller applying a pulse wave in said simulated therapy zone with a simulated in vivo pressure differential chosen from among the group comprising circulatory, lymphatic or respiratory;
    a pressure force sensor embedded in said medium material and adapted for sensing a pressure force effect including fluid pressure source amplitude and frequency therein;
    an output connected to said pressure force sensor and adapted for providing output corresponding to said sensed pressure force effect and including amplitude and frequency of pressure waves in said medium material;
    wherein said medium material comprises a synthetic gel; and
    wherein said synthetic gel comprises a synthetic material with soft-tissue characteristics.

2. The system according to claim 1, which includes:
    laser optical sensors mounted on said container and configured for projecting a laser energy beam into said medium material and providing an output representing frequency and amplitude of said pressure waves in said medium material;
    said laser optical sensors having orientations relative to said medium material, said sensor orientations being user-adjustable; and
    said controller connected to said laser optical sensor, said controller programmed for: generating liquid pressure pulses in said medium material with said pump discharge; controlling the amplitude and frequency of said liquid pressure pulses; providing an output modeling simulated in vivo blood pressure including frequency and amplitude parameters in said medium material based on the input received from said laser optical sensor; and controlling said liquid pressure pulse frequency and amplitude based on preprogrammed parameters.

* * * * *